United States Patent [19]
Dale

[11] Patent Number: 5,141,861
[45] Date of Patent: * Aug. 25, 1992

[54] METHOD OF USE OF A MULTI-STAGE REACTOR-SEPARATOR WITH SIMULTANEOUS PRODUCT SEPARATION

[75] Inventor: M. Clark Dale, West Lafayette, Ind.

[73] Assignee: Bio Process Innovation, Inc., West Lafayette, Ind.

[*] Notice: The portion of the term of this patent subsequent to May 12, 2004 has been disclaimed.

[21] Appl. No.: 372,253

[22] Filed: Jun. 27, 1989

Related U.S. Application Data

[63] Continuation of Ser. No. 45,640, Apr. 24, 1987, abandoned, and a continuation-in-part of Ser. No. 548,531, Nov. 3, 1983, Pat. No. 4,665,027.

[51] Int. Cl.⁵ .............................................. C12P 7/14
[52] U.S. Cl. ............................... 435/162; 203/DIG. 6; 203/DIG. 13; 426/494; 435/315; 435/151; 435/813; 435/819
[58] Field of Search ............... 435/161, 162, 313, 314, 435/315, 151, 813, 819, 288; 426/494; 203/DIG. 6, DIG. 13, 19; 436/55; 210/603, 632

[56] References Cited

U.S. PATENT DOCUMENTS

| | | | |
|---|---|---|---|
| 2,123,463 | 1/1938 | Effront | 435/819 X |
| 2,383,176 | 8/1945 | Willkie | |
| 2,440,925 | 5/1948 | Boeckler | 426/13 |
| 2,804,427 | 8/1957 | Suriano | 203/261 X |
| 4,665,027 | 5/1987 | Dale et al. | 435/162 X |
| 4,978,616 | 12/1990 | Dean, Jr. et al. | |
| 4,978,618 | 12/1990 | Kalina | 435/819 X |

OTHER PUBLICATIONS

J. H. Janssens et al., Biotechnology & Bioengineering, vol. 26, pp. 1–5, (1984), *Ethanol from Whey: Continuous Fermentation with Cell Recycle*.

Primary Examiner—Robert J. Warden
Assistant Examiner—Amalia Santiago
Attorney, Agent, or Firm—Fleit, Jacobson, Cohn, Price, Holman & Stern

[57] ABSTRACT

A multi-stage reactor-separator for the fermentative production of volatile inhibitory products from non-volatile substrate includes a stirred tank reactor and a packed or tray-type gas-liquid contacting column separator. Each reactor and separator form a stage and a plurality of stages may be stacked into a tower, or otherwise placed to operate consecutively, forming a reactor-separator in which stages having gas flowing cocurrent to the liquid flow in the separator portion form an enriching section, and stages having gas flowing countercurrent to the liquid flow in the separator portion form a stripping section. In a method of using the reactor-separator, a volatile fermentation product is produced and simultaneously separated into a gas phase.

7 Claims, 8 Drawing Sheets

METHOD OF USE OF A MULTI-STAGE REACTOR-SEPARATOR WITH SIMULTANEOUS PRODUCT SEPARATION

RELATED APPLICATION

This application is a continuation of Ser. No. 045,640, filed Apr. 24, 1987, now abandoned, which is a continuation-in-part of U.S. patent application Ser. No. 548,531, filed Nov. 3, 1983 now U.S. Pat. No. 4,665,027 issued May 12, 1987. The entire disclosure of the parent application is incorporated herein by reference.

FIELD OF THE INVENTION

The invention relates to fermentation apparatus for production and separation of volatile products, and a method for separation of fermentation products.

BACKGROUND OF THE INVENTION

The production of inhibitory products or by-products during fermentation has previously retarded cell growth and reaction rates and increased cell death rate. For ethanol fermentation, several simultaneous reaction-separation processes have been suggested, including systems based on a continuous stirred tank reactor (CSTR). The ATPAL process (Spear, Food Eng. (1981) 2, 85) provides for continuously withdrawing a portion of a fermenting mixture from a CSTR, flash vaporizing the portion to a vapor and liquid stream, recovering product from the vapor stream and returning the liquid stream to the CSTR. A similar system has been designed and operated by Alpha Laval (the "Bio-Still" reactor, 1983 product literature). Other systems, e.g. those suggested by Ramalingham and Finn (Biotechnol. Bioeng. (1977) 19, 583), Cysewski and Wilke (Biotechnol. Bioeng. (1977) 19, 1125), and Neves (U.S. Pat. No. 4,425,433), suggest operation of the CSTR under a vacuum. This results in substantial ethanol separation from the CSTR and pulling the ethanol with overhead vapors into the vacuum pump. Carbon dioxide generated by the fermentation also leaves with the vapors. With these CSTR systems, non-volatile fermentation inhibitors, both fermentation by-products and feed inputs, may accumulate and be retained in the system. This problem is particularly acute with such feeds as whey (having a high mineral content) or converted cellulosic residues (which may contain a variety of non-fermentables). The bleed stream from the CSTR must be high enough to keep the level of inhibitors low enough to maintain cell viability. As the bleed stream contains substrate and product in the same concentration as in the reactor, this bleed stream may represent a considerable loss.

The use of an organic second liquid phase has been suggested by Albersson (Biotechnol. Bioeng. (1980) 12, 2393), Minier and Goma (Biotechnol. Bioeng. (1982) 24, 1565), Dreyfus (U.S. Pat. No. 2,053,770), and Tedder (U.S. Pat. No. 4,510,242). The contemplated methods require intimate contacting of two liquid phases (followed by phase separation), and recovery of product from the organic phase. Although such systems may speed the reaction, many difficult contacting and separation steps are needed to obtain a pure organic product. In addition, many employed organic solvents are poisonous to cells.

It has been found that, by using a stripping-gas phase in an immobilized cell reactor-separator (ICRS), high reaction rates and near-complete separation are attainable in a plug flow reactor. The ability to run such a reactor at atmospheric pressure and ambient temperature was also established. In a two column reactor, a cocurrent enrichment section (in which the product level increased in the broth) is followed by a stripping section (in which the product is stripped by a countercurrently flowing gas stream). In the ICRS of U.S. Pat. No. 4,665,027, the packing is designed to provide free passage of the stripping gases, but insoluble solids or very viscous liquids may sometimes clog the gas passages, and the presence of cell growth on the packing might have the same clogging effect. The packing in the ICRS is designed to accomplish three simultaneous objectives, 1) hold a high cell density, 2) contact the cells with the fermentation broth (which is facilitated by a high liquid holdup), and 3) contact the broth with the stripping gas to provide efficient mass transfer of the volatile product into the gas phase with a modest pressure drop.

If a liquid continuous reactor system with gas contacting is carried out in a perforated-plate bubble column with bubbles entering through a sparger in the bottom of the column, design problems, including: 1) a high degree of axial mixing in the columns, 2) foam generation, 3) surging and pulsing of the gas phase, and 4) a high gas phase pressure drop, are encountered. A simple standard tray tower (as used in distillation) also cannot be used, since tray spacing is generally from 12 to 20 inches to reduce liquid carry-over, and the liquid level on each stage is about 0.5 to 1.5 inches. This results in a liquid hold-up of from 1 to 6% in the column, requiring a very large distillation tower to achieve the required liquid residence time to complete the reaction. The low liquid holdup on a distillation column tray results in very short liquid residence times and consequently little reaction. Johnson et al. (U.S. Pat. No. 4,327,184) employ low temperature gas stipping of exit broth from a fermenter using a distillation column, but do not contemplate that any reaction can take place in the distillation column (due to the very short residence time in the column). Other drawbacks of known apparatus include: 1) a high pressure drop of from 1 to 2 inches of water per stage, 2) liquid channeling, 3) foam generation, and 4) inability to allow cocurrent gas flow.

SUMMARY OF THE INVENTION

A multi-stage reactor-separator for fermentative production of volatile inhibitory product from non-volatile substrate preferably includes stages cascaded in series in a vertical arrangement allowing liquid to flow through the system without pumping. In a stage of the apparatus, product is formed in a liquid fermentation phase in a stirred tank reactor portion by the action of biological catalyst or cells upon the substrate. The product-containing liquid phase is then contacted by a stripping gas phase as the liquid phase flows through a gas-liquid contacting separator portion of the stage into the reactor portion of a subsequent stage.

In a preferred embodiment, stages are assembled vertically into two basic reaction sections: an enriching section and a stripping section. Feed broth containing substrate and nutrients is fed to a reactor portion of a first stage of the enricher. Substrate is converted to product and the product distributes between the broth and the stripping gas in a gas-liquid contacting separator column of each stage. Cocurrent gas and liquid flow in the separator column of the enriching section promotes an increase in product concentration in the liquid broth (as it passes from stage to stage) as well as in the stripping gas stream. The liquid fermentation broth leaving the enriching section is fed to the stripping section where the broth is contacted countercurrently by a stripping gas while the remaining substrate is converted to product. The liquid product concentration in the stripping section is reduced by stripping the product into with gas flowing countercurrent to the liquid flow, allowing high reaction rates and complete conversion of the substrate. Effluent from the stripper is characterized by low concentrations of both product and substrate.

High reaction rates in the system are achieved by maintaining a low product concentration and a high biological catalyst or cell density in the fermentation broth. A high cell density is maintained in each stage either by immobilizing the cells on pellets or other solid medium or by recycling free cells from the effluent. The production of ethanol from lactose, glucose and/or starch are typical examples of use of the invention.

The invention is particularly useful in carrying out product-inhibited fermentations, such as in the bio-production of ethanol, acetone, acetic acid, butanediol, or butanol. More particularly the invention relates to a continuous multi-stage reactor-separator (MSRS) having a unique four phase system, incorporating (1) an inert stripping gas phase, (2) liquid fermentation broth, (3) optional solid reactor internals, and (4) biological catalyst or cells, for separating a volatile inhibitory metabolite from a fermentation medium. Apparatus of the invention includes a stirred liquid reactor tank portion and a gas-liquid contacting separator portion, allowing fermentation in the stirred tank portion and separation of volatile products in the gas-liquid contacting portion. A multi-stage reactor-separator of the invention includes two or more stages in series, a stripping gas stream moving through the gas-liquid contacting portion of each stage. At least one stage of an MSRS is an enricher section having cocurrent gas-liquid flow in the separator portion, and at least one stage is a stripper section having countercurrent gas-liquid flow in the separator portion. Alternatively, the reactor-separator may have either the enricher section or the stripper section configured as one or more stages (as described) and the other of the sections configured as a packed column, as described in U.S. Pat. No. 4,665,027.

In a preferred embodiment of the MSRS, feed broth enters an enriching section in which one or more stages are operated in series having cocurrent gas-liquid flow, followed by feeding liquid effluent fermentation broth from the enriching section to a stripping section having one or more stages operated in series using countercurrent gas-liquid flow for stripping. This arrangement provides a system characterized by an effluent low in both volatile product and substrate. Moreover, a purified product stream containing no fermentation substrate or cells is recovered from the gas stream exiting the enricher and stripper sections of the reactor system. A preferred multi-stage reactor separator system of the invention includes a plurality of stages in series with a high cell density on each stage and separation of inhibitory volatile product, allowing high reaction rates to be maintained.

An MSRS with gas phase stripping of volatile fermentation product has the ability to handle viscous feeds or feeds with insoluble solids. The MSRS also has the advantage of decoupling the system by removing the interdependence of the reaction and the separation. Thus, the reactor portion of each stage may be designed separately to ensure complete and rapid fermentation of the substrate, while the separator portion may similarly be optimized to provide a high gas-liquid contact area, a low pressure drop, and low fouling or clogging tendencies.

An object of the invention is to provide a method and apparatus for a quick and complete conversion of substrate to volatile product in a reactor with simultaneous product removal.

NOMENCLATURE

The following nomenclature is used herein:
F = liquid feed rate (liter/hour)
P = product concentration (gram/liter)
$P_{max}$ = maximum product concentration (gram/liter)
$P_o$ = outlet product concentration (gram/liter)
$K_p$ = ethanol inhibition constant (gram/liter)
$K_{s1}$ = substrate saturation constant (gram/liter)
$K_{s2}$ = substrate inhibition constant (gram/liter)
S = substrate concentration (gram/liter)
$S_1$ = inlet substrate concentration (gram/liter)
$S_o$ = outlet substrate concentration (gram/liter)
$x_{i,j}$ = liquid molar concentration of component i on stage j
$x_s$ = cell density (grams dry weight/liter)
$v_{max}$ = maximum specific ethanol productivity (gram ethanol/gram cell-hour)
$y_{i,j}$ = gaseous molar concentration of component i in gas leaving stage j
G = molar flow of gas (mole/hour)
$G_i$ = inlet molar flow of gas (mole/hour)
$G_o$ = outlet molar flow of gas (mole/hour)
$H_c$ = height of separation column on stage
$H_{st}$ = height of stage
$ID_{st}$ = inner diameter of stage
$ID_c$ = inner diameter of gas-liquid contacting column
L = molar flow of liquid (mole/hour)
$L_i$ = inlet molar flow of liquid
$L_o$ = outlet molar flow of liquid
G/L = molar flow ratio of gas to liquid
t = average residence time of fluid in the reactor ($V_r/F$)
r = reaction rate (gram product/liter-hour)
$V_{st}$ = total liquid holdup volume on a single stage
$V_r$ = total reactor volume

BRIEF DESCRIPTION OF THE DRAWINGS

FIG. 1b is a cross-sectional view taken on line 1b—1b of FIG. 1a.

DETAILED DESCRIPTION OF THE INVENTION

A multi-stage reactor-separator (MSRS) of the invention includes both a reactor portion and a separator portion in each stage. Each stage has an agitated liquid reactor portion which operates as a continuous stirred tank reactor (CSTR). Liquid fermentation broth containing nutrients and substrate is fed into the CSTR portion of a stage either from the prior stage or as direct feed. The fermentation follows standard fermentation kinetics and, since the tank contents are agitated, the broth is characterized by a uniform concentration of product and reactants. High reaction rates may be attained by maintaining a low concentration of inhibitory product and/or by maintaining a high concentration of biological catalyst and/or whole cells in the reactor. High biological catalyst or cell concentration (or density) may be attained by any method known in the art, including catalyst immobilization in or on a mobile or non-mobile support matrix, such as pellets, beads, or extended solid surface, or by using catalyst recycle by recovering a concentrated stream of biological catalyst from the reactor effluent and returning this stream to the reactor inlet using, for example, centrifugation and membrane filtration. Appropriate biological catalyst or cells include enzymes and microorganisms known to one skilled in the art, for example, yeast cells. Thorough mixing occurs even if the catalyst or cells are immobilized on a supporting matrix.

The outflow, which may be an overflow, from the reactor (CSTR) portion of a stage is directed into a gas-liquid contacting separator portion of the stage through which gases and vapors are contacted with liquid outflow broth from the reactor portion. The outflow broth contains biological catalyst or cells which flow with the outflow broth into the separator portion. This gas-liquid contacting separator portion may contain random or structured column packing (i.e. Berl saddles, Pall rings, etc.) or standard tray type construction may be used. The gases may travel either cocurrently with or countercurrently to the overflow broth in the gas-liquid contacting column. Gas may be bubbled through the CSTR to enhance gas/liquid contact, if required.

Figure 1A:
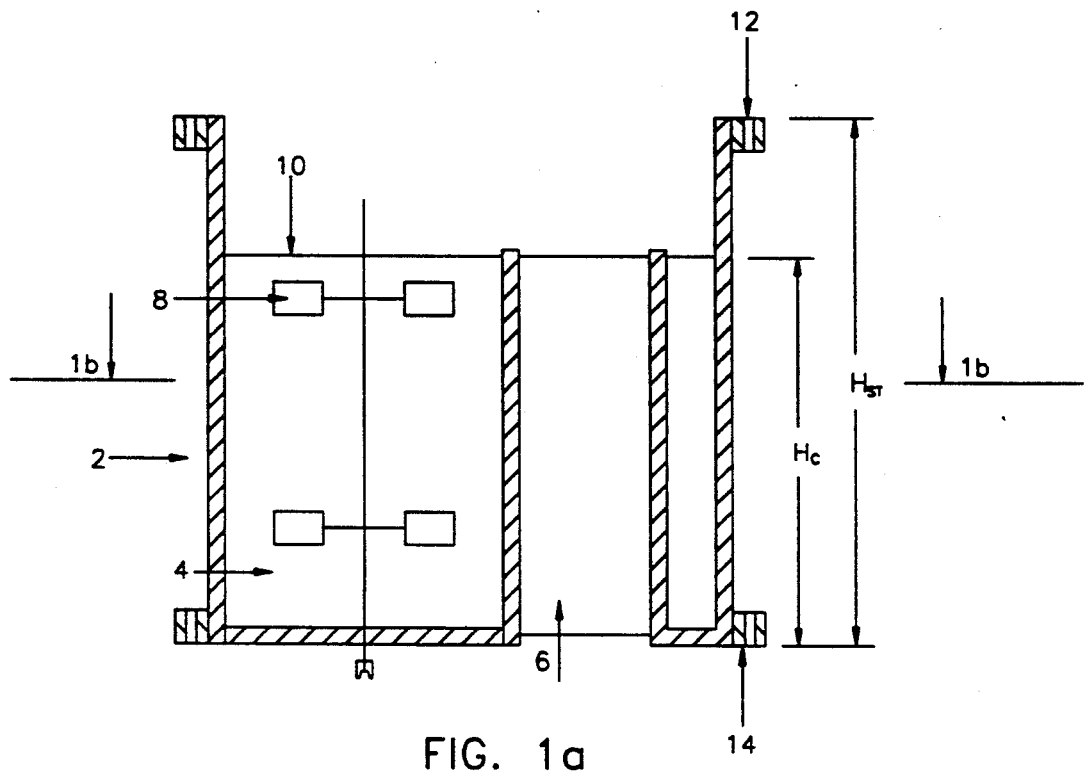
FIG. 1a is a longitudinal cross-sectional view taken on a vertical plane through a diameter of a single stage of a reactor of the invention.
Figure 1B:
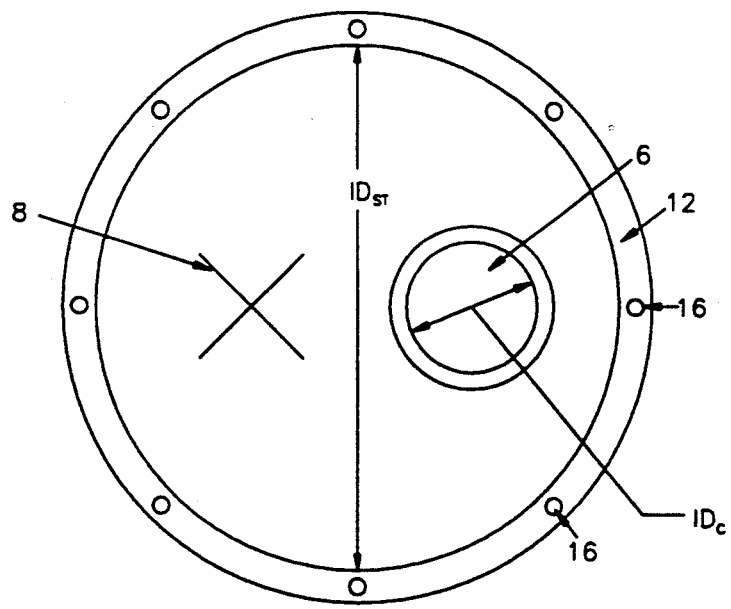

Referring to the figures, in which like numerals represent like parts, FIG. 1 shows a preferred embodiment of stage 2, useful for practicing the invention, in which gas phase stripping of volatile inhibitory fermentation products or by-products takes place. Stage 2 comprises reactor tank 4 which surrounds packed or tray-separator column 6, the column being placed off-center within tank 4. The contents of tank 4 are stirred, or otherwise agitated by, for example, motorized paddle stirrer 8. In a preferred arrangement, shown in FIGS. 2 and 3, a plurality of stages 2 are typically stacked to form a tower, separator column 6 is placed within the body of reactor tank of each stage 2 in a different position relative to each column 6 in the stages above and below. Thus, column 6 is in a rotationally offset position from adjacent stages above and below stage 2, so that effluent leaving a separator column 6 falls into the next lower stirred tank reactor 4 and does not fall directly into the next lower separator column portion 6. FIG. 1b shows one example of a position of column 6 in reaction tank 4. Other types of stirrer or agitator may be used instead of a motorized paddle stirrer. Liquid level 10 is such that tank 4 is filled with feed broth, and overflow (including biological catalyst or cells) passes into column 6, effluent from column 6 being discharged into tank 4 of the next lower stage. Flanges 12, 14 extend respectively from the top and bottom circumferences of tank 4 to facilitate stacking of the tanks. Bolts 16 secure the flanges.

Figure 2:
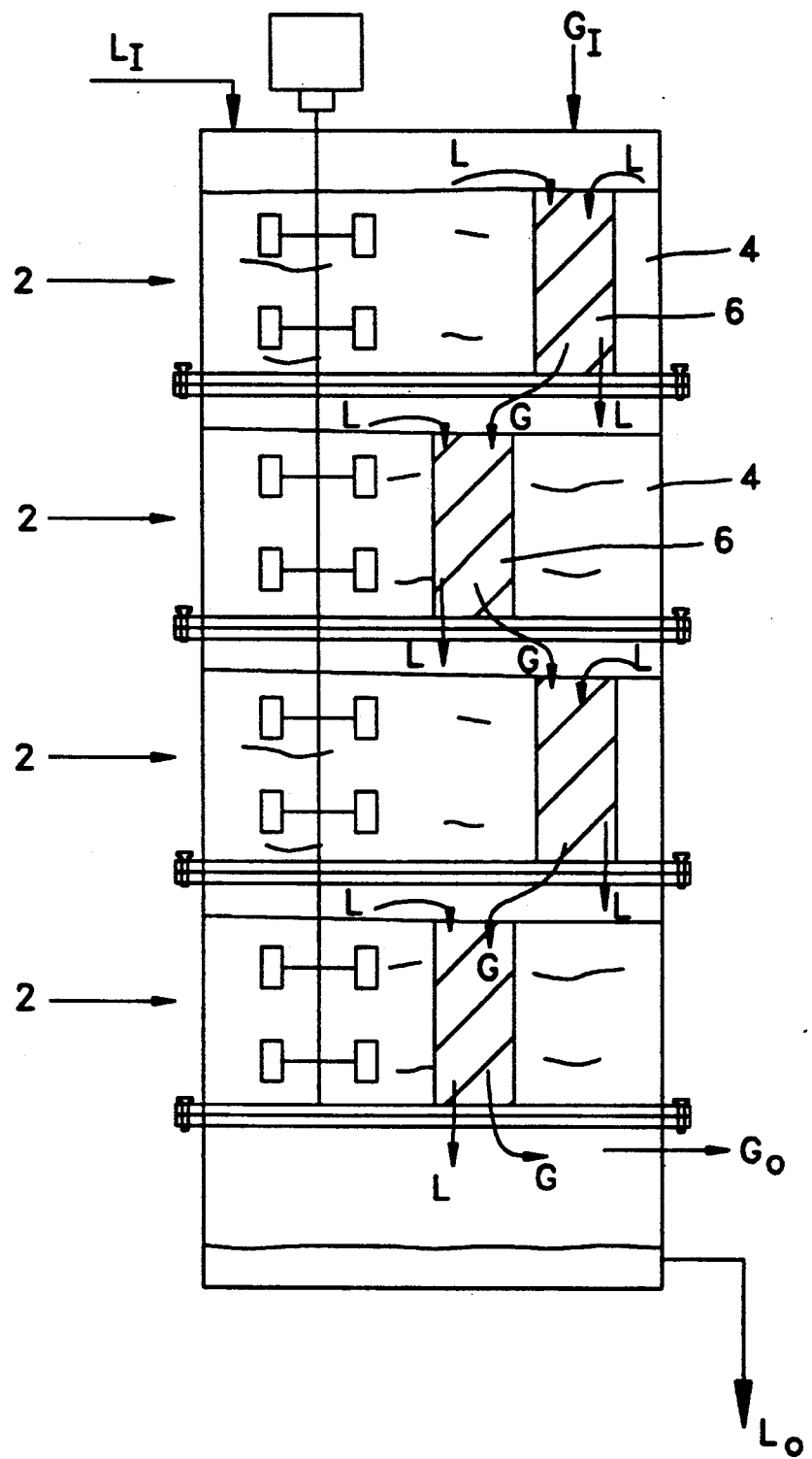
FIG. 2 is a schematic diagram of a four-stage reactor of the invention showing cocurrent gas-liquid flow.
Figure 3:
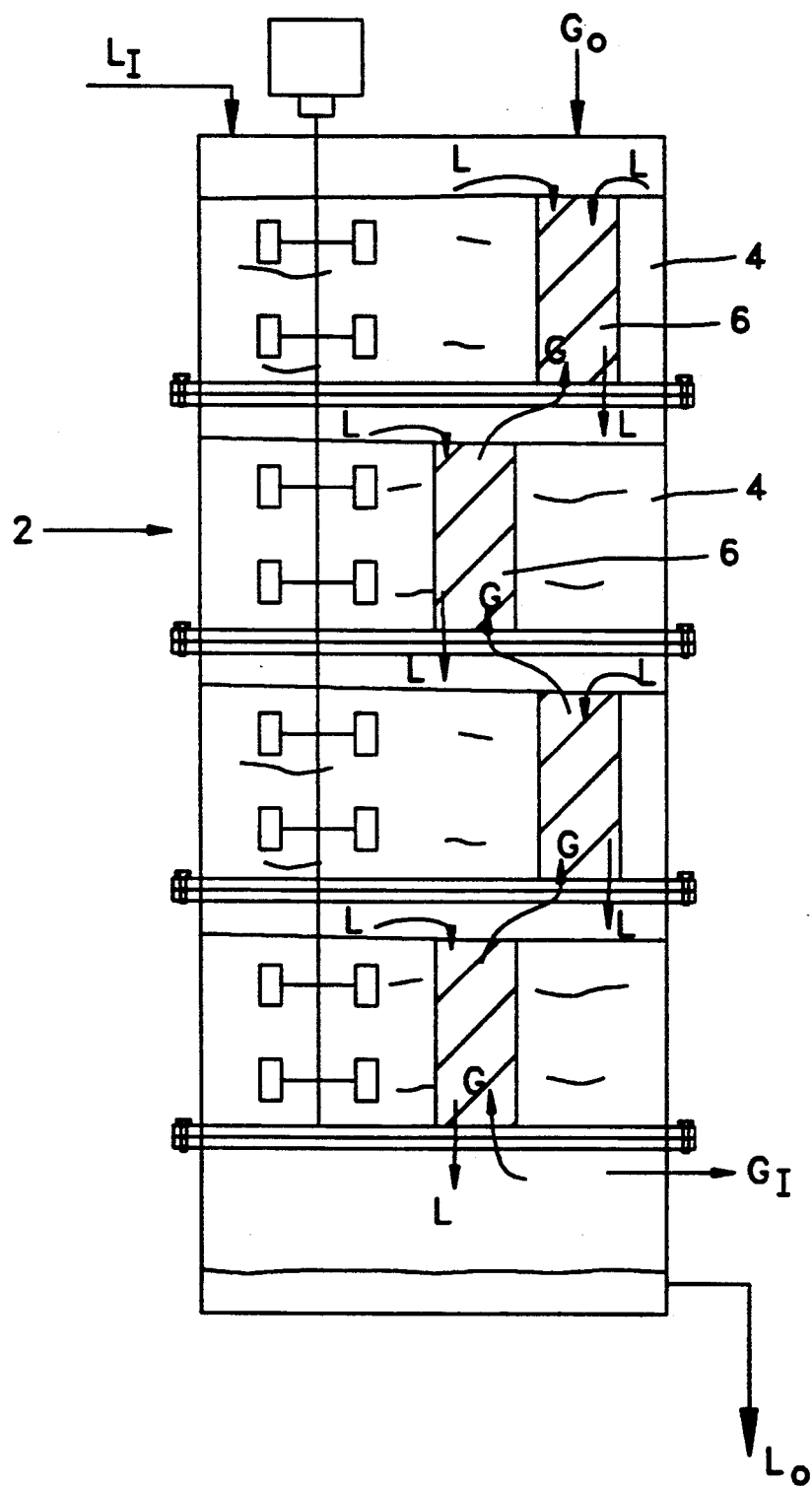
FIG. 3 is a schematic diagram of a four-stage reactor of the invention showing countercurrent flow.
Figure 8:
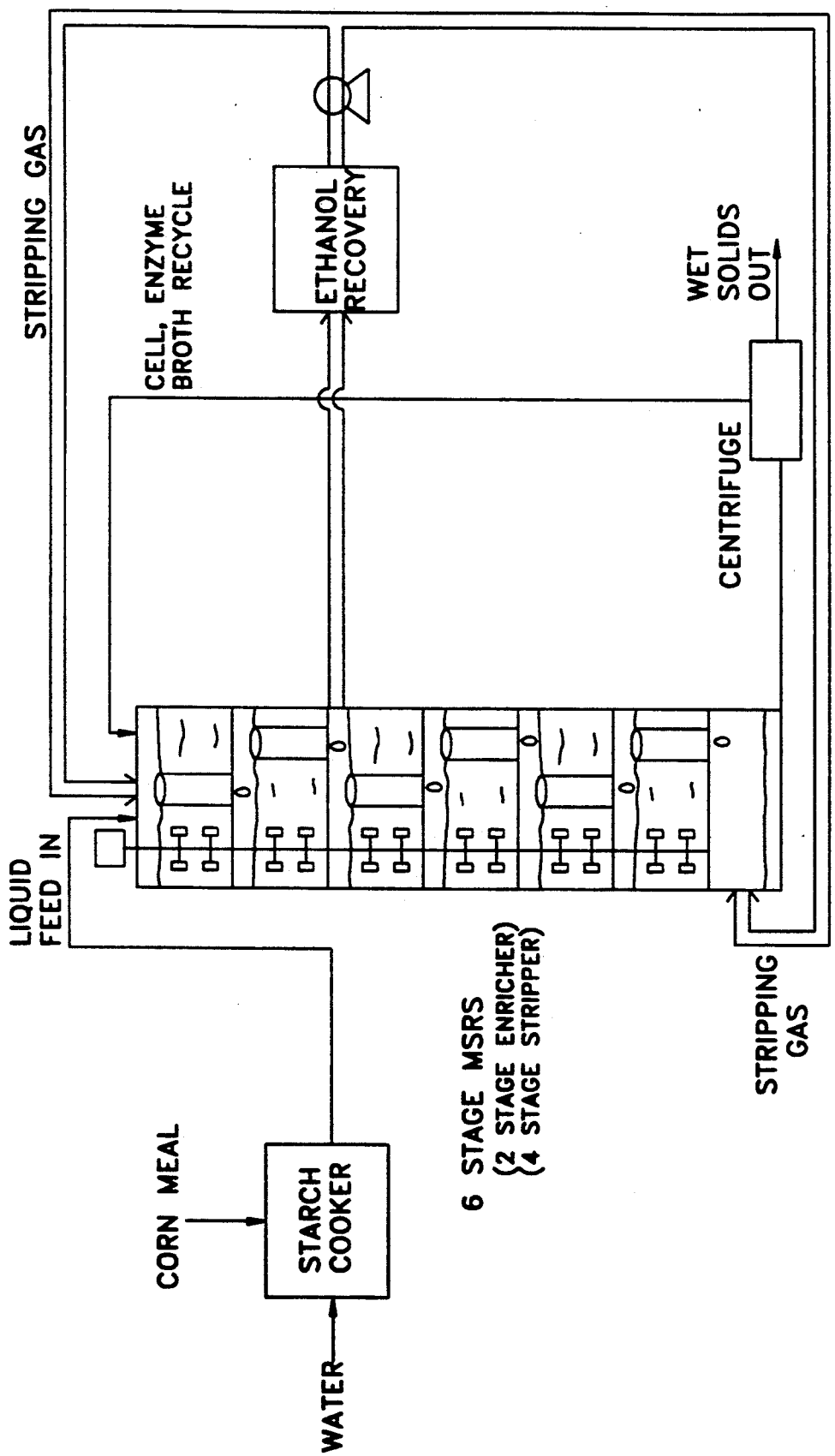
FIG. 8 is a schematic process diagram for a 6-stage MSRS (Example 3).

In a preferred embodiment, the MSRS consists of a plurality of flanged reactor/separator stages 2 (shown in FIG. 1) which are assembled into an enricher-stripper tower, as shown schematically in FIG. 2 (enricher) and FIG. 3 (stripper). In a preferred use, as shown in FIG. 8, the enricher is placed on top of, and feeds downward into, the stripper. Each reactor stage 2 includes a liquid continuous stirred tank reactor 4 (having liquid input from the separator section 6 of the stage above) with liquid overflow to a gas-liquid contacting separator section 6. Liquid exiting the stage feeds to the reactor portion 4 of the stage below, the liquid flow allowing intimate gas-liquid contact in the separator section, gas flow being either downwards (enricher) or upwards (stripper) as the liquid flows downward into the reactor portion of the stage below. Thus, each stage is essentially a combined stirred tank reactor 4 and gas-liquid contacting separator column 6. A separator column 6 may have an internal structure of either a packed column or a tray-type column, a packed column allowing a lower pressure drop and fewer problems of foam generation, whereas a tray-type column is less likely to clog with solids. The liquid leaving the bottom of the gas-liquid contacting separator column 6 falls into the reactor portion 4 of the next lower stage and does not continue directly down the separator column 6 of the next lower stage. The MSRS provides a reactor-separator system allowing a low pressure drop, good gas-liquid separation through the use of standard gas-liquid separation column internals, a liquid continuous reactor volume which can be varied to design specifications, and no axial mixing of liquid between reactor stages in the tower.

The MSRS, using flanged reactor-separator stages, as shown in FIGS. 1 to 3, at least partially decouples the reaction and separation. The reacting volume of the reactor section may be varied by varying the height ($H_{st}$) and the diameter ($ID_{st}$) of the section, and the total reacting volume can then be determined by the number of stages in the enricher and stripper columns. The diameter of the separator column ($ID_c$) may also be optimized for best separation performance. The separator column may be of either packed or tray construction. A packed column is preferred.

For a gas-liquid contacting separator column of a single reactor section having M equilibrium stages, a system of steady state equations may be written for a series of N reactor sections in a single tower. The composition of the liquid and the vapor in the countercurrent stripping separator section of the MSRS may be calculated (assuming no reaction), using the following equation:

$$L(x_{i,j-1}-x_{i,j})+G(Y_{i,j+1}-Y_{i,j})=0 \qquad [1]$$

where the initial liquid feed is the composition of stage $N+1$, and N is the number of separator stages in the column. The volatile components will be distributed between the gas and liquid streams according to equilibrium driving forces. The steady state composition of each of the L stirred tank reactors can be given as:

$$x_{i,j} = x_{i,j-1} + (V_{st}/L)r_i \quad [2]$$

This set of equations can be solved using standard exact methods for determining compositions in separation columns. The relaxation technique of Jelinek et al. (Chem. Eng. Commun. (1976) 2, 79) is particularly helpful in achieving convergence of sets of equations of this type.

The MSRS can be operated at any desired temperature and pressure. If a yeast fermentation of sugars to ethanol is being carried out, temperatures will largely be determined by the thermal activity region of the yeast, generally 25° C. to 40° C. Operating with thermophilic yeast cells at higher temperatures is advantageous. When an operating temperature has been set, an operating pressure is determined. In general, operation at atmospheric pressure will allow lower capital and operating costs than vacuum or high pressure operation. As shown in U.S. Pat. No. 4,665,027, while operation at reduced pressures can reduce the required gas flow rates, actual volume of the gas stream remains relatively constant. Thus, the gas phase stripping reactors of U.S. Pat. No. 4,665,027 and the present application accomodate a high ratio of gas to liquid flow volumes. Other types of cells or biological catalysts may be used alternatively to yeast, as described in U.S. Pat. No. 4,665,027.

Figure 4:
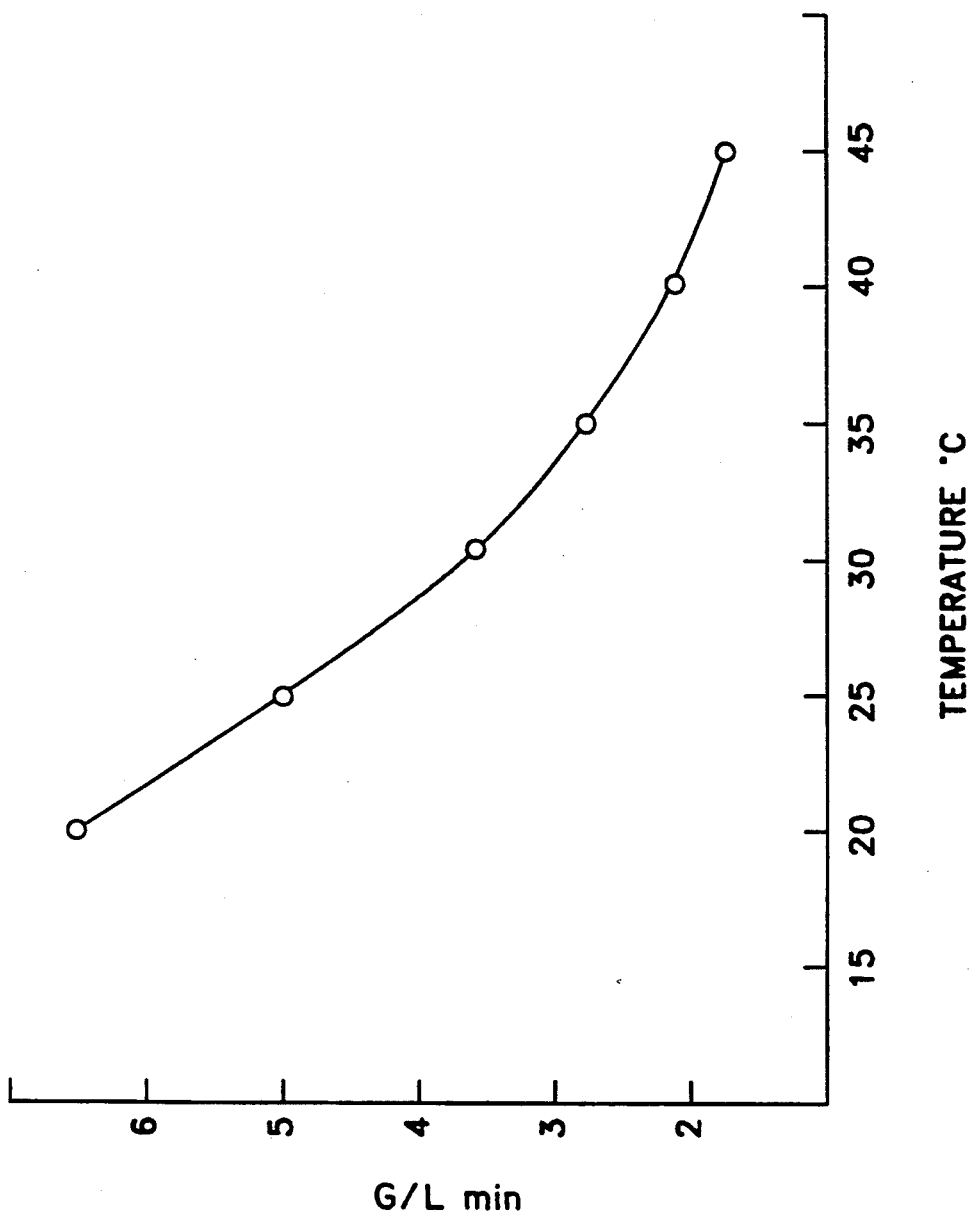
FIG. 4 is a graphical representation of changes in inert gas molar flow ratio (G/L) as a function of temperature.

When temperature and pressure have been determined, the required gas flow to reduce the concentration of volatile component can be determined. For ethanol fermentation in the stripper section of an MSRS, FIG. 4 shows the required inert gas to liquid molar flow ratio (G/L) to reduce the outlet ethanol concentration to less than 1% of the inlet concentration as a function of temperature. The required gas flow ratio drops by a factor of about 2 with each 10° C. increase in temperature. This indicates that gas circulation costs are reduced if higher operating temperatures can be tolerated by thermophilic type organisms or biological catalysts. As shown in U.S. Pat. No. 4,665,027, when temperatures reach about 85° C., no additional stripping gas is required.

The temperature of the stirred tank reactor may be controlled by cooling coils in the tank if the heat of reaction is large enough to cause substantial heating on a stage. The gas contacting between the stages will tend to cool the liquid broth with the temperature largely controlled by the saturation temperature of the circulating gas stream. The temperature of the MSRS may be easily controlled by simple adjustment of the inlet saturation temperature of the inlet gas to the enriching and stripping segments of the MSRS.

Figure 5:
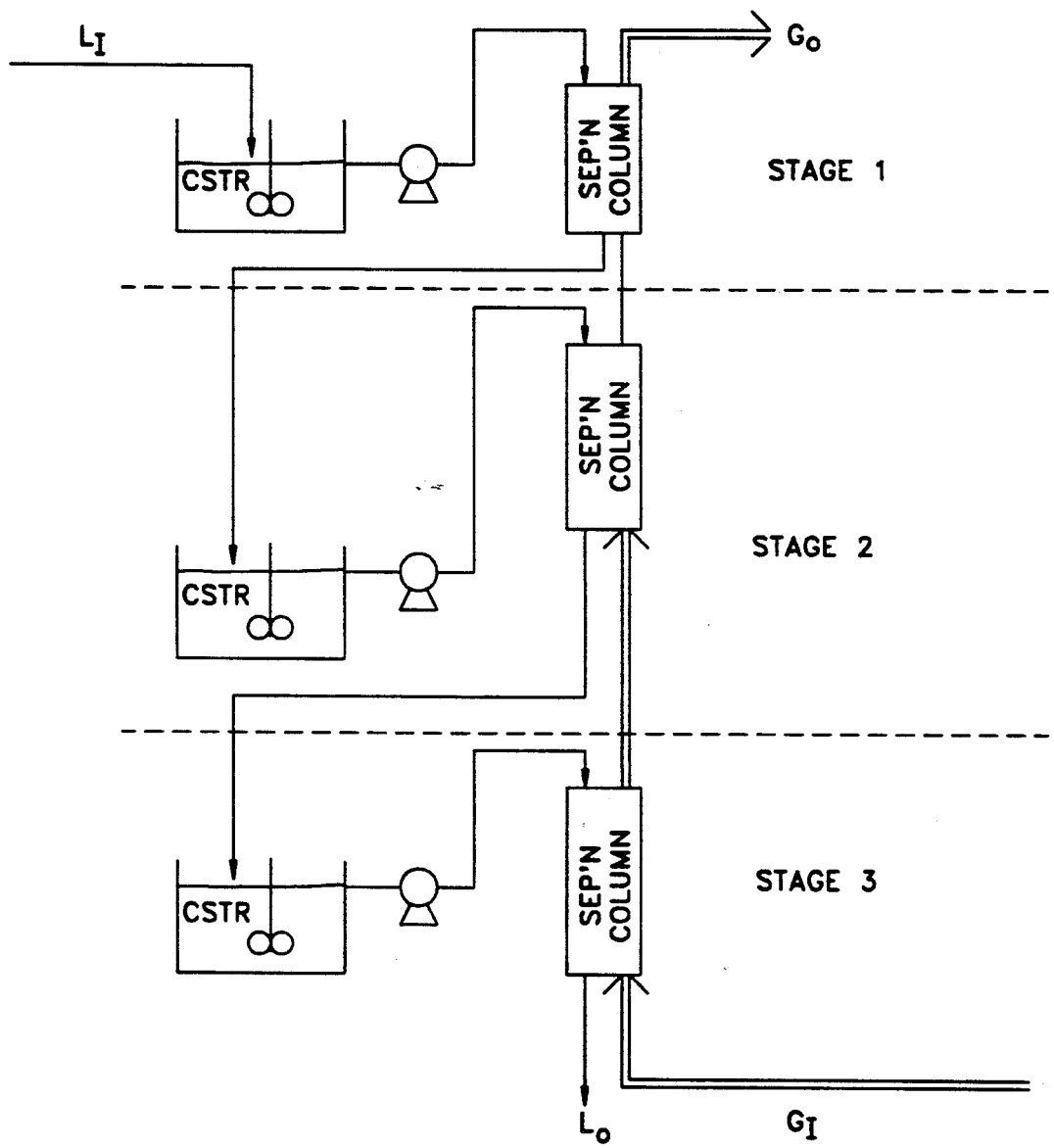
FIG. 5 is a schematic diagram of a 3-stage stripping section of the invention showing countercurrent flow column separators separated from reactors of each stage.

Other arrangements of the apparatus may equally well be used. The separator may alternatively be adjacent to, or separate from the reactor when it receives overflow liquid from the reactor portion of the stage. A "stage" may be a single unit, as shown in the preferred embodiment, or may take the form of a reactor and a separator each standing alone, as shown, for example by the countercurrent stripper of FIG. 5. An enricher section, having cocurrent gas flow in the separator section may be similarly configured. The "stages" may alternatively be constructed adjacent to or separate from each other, instead of in the preferred arrangement, shown in the Figures, in which the enricher sections are stacked above the stripper sections. In other embodiments a stage may be used for the enricher, and a column (as described in U.S. Pat. No. 4,665,027) may be used for the stripper, or the enricher may be a column and the stripper may be a stage. Other variations will be apparent to one skilled in the art.

The agitation of the stirred tank reactor may be achieved by introducing some portion of the stripping gas stream entering the stage into the stirred tank reactor in place of, or in addition to, using a stirrer. Additional compression of the gas stream is required but there are further beneficial effects of cooling and providing gas phase nutrients (e.g. oxygen) to the reactor.

EXAMPLE 1

To determine use of the MSRS, the production of ethanol from lactose is modeled using equations [1] and [2], solved using the reaction rate expression and constants shown in Table 1, assuming that each stage has the same reacting liquid volume. Table 1 describes the reaction kinetics of *Kluyveromyces fragilis* yeast cells, strain NRRL 2415.

TABLE 1

Reaction rate expression:

$$r = x_s \, v_{max} \, \exp(-k_p P) \left( \frac{S}{K_{s1} + S} \right)$$

where:
$x_s = 50$ g/l
$v_{max} = 1.5$ gram ethanol/gram cell-hr
$K_p = 0.035$ gram/liter
$K_{s1} = 6.6$ gram/liter
r = gram ethanol/liter-hr For this example, a typical stage has a diameter of 60 cm., a liquid level on the stage of 60 cm., and a packed bed gas-liquid contacting overflow column of 21 cm. diameter, which corresponds to a working reactor volume of 149 liters per stage. A molar gas to liquid flow ratio (G/L) of 1.0 is used in the enricher while a G/L ratio of 6.0 is used in the stripper. Operation of the MSRS is at atmospheric pressure and 32° C. A cell density of 50 g/l dry weight cells is used on each stage as shown in Table 1. This cell density is achieved by recycle or immobilization of the cells. The size of the reactor may be varied for different flow rates or feed concentrations. Measurement of cell density is described in U.S. Pat. No. 4,665,027.

TABLE 2

Reactor Performance as a Function of Reactor Design

| | Reactor | Performance Parameters |
|---|---|---|
| 1. | 1 stage CSTR | $S_o$ = 1.5 g/l |
| | | $P_o$ = 89.2 g/l |
| | | r = 0.61 g/l/hr |
| | | t = 146.0 hr |
| 2. | 3 stage CSTR | $S_o$ = 1.8 g/l |
| | | $P_O$ = 89.1 g/l |
| | | r = 3.71 g/l/hr |
| | | t = 24 hr |
| 3. | 5 stage CSTR | $S_o$ = 4.0 g/l |
| | | $P_o$ = 88.0 g/l |
| | | r = 4.86 g/l/hr |
| | | t = 15 hr |
| 4. | 5 stage MSRS | $S_o$ = 1.5 g/l |

| | Reactor | Performance Parameters |
|---|---|---|
| | (2 stage enricher) | $P_o$ = 8.4 g/l |
| | (3 stage stripper) | r = 35.5 g/l/hr |
| | | t = 2.48 hr |
| 5. | 8 stage MSRS | $S_o$ = 1.5 g/l |
| | (3 stage enricher) | $P_o$ = 4.8 g/l |
| | (5 stage stripper) | r = 41.3 g/l/hr |
| | | t = 2.16 hr |
| 6. | 10 stage MSRS | $S_o$ = 1.25 g/l |
| | (4 stage enricher) | $P_o$ = 3.5 g/l |
| | (6 stage stripper) | r = 42.2 g/l/hr |
| | | t = 2.12 hr |

Reactor parameters are shown in Table 1.
Inlet substrate concentration: $s_i$ = 180 g/l lactose
For the MSRS: G/L (enricher) = 1.0 and G/L (stripper) = 6.0

Figure 6:
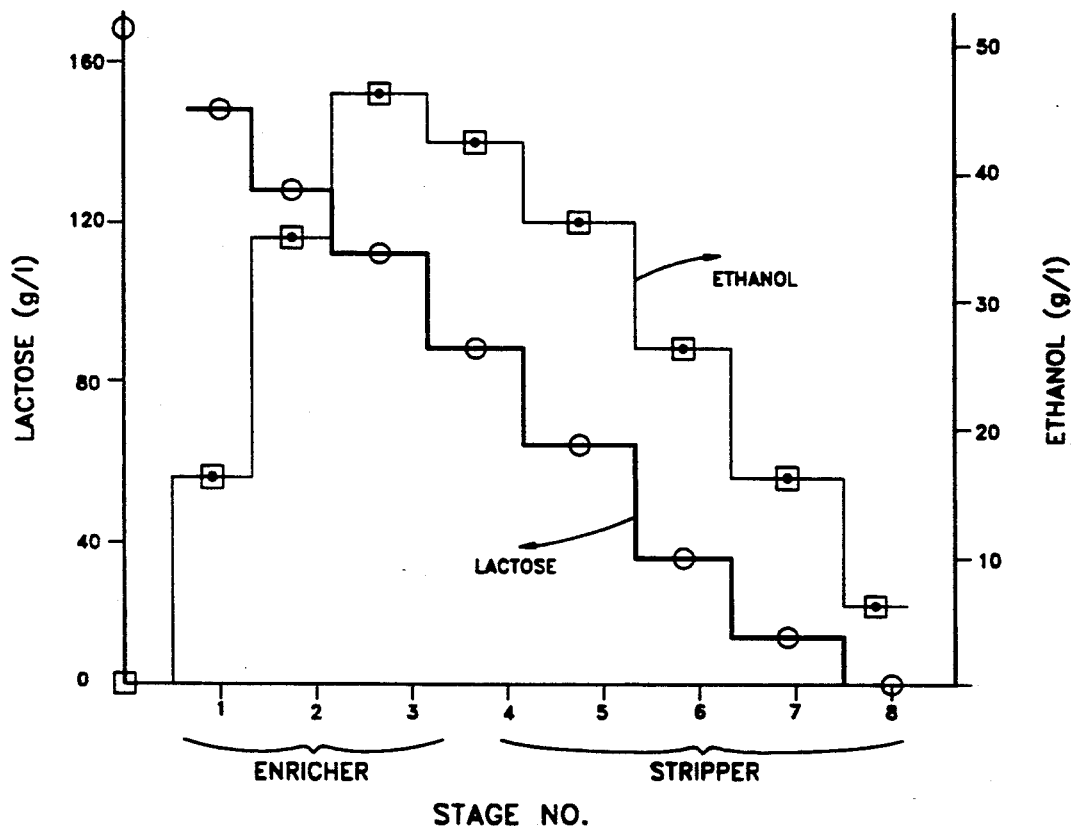
FIG. 6 is a graphical representation of stage profiles for an 8-stage MSRS (Example 1).

The application of the MSRS to a lactose to ethanol fermentation with an 18% lactose feed is compared to single and multiple staged stirred tank reactors with no gas stripping. Table 2 shows the average residence time and outlet ethanol concentration for various reactor configurations. There is a substantial decrease in residence time, to substantially less than 3 hours, using an MSRS in which product separation is incorporated. Comparative examples using a CSTR show that a 5-stage CSTR completes the reaction with a residence time of 15.0 hours while the 5-stage MSRS gives a more complete conversion (shown by lower outlet substrate concentration, $S_o$) in 2.48 hours (a 600% increase in performance). Increasing the number of stages in the MSRS allows the residence time to be reduced slightly to 2.16 hours with 8 stages, and 2.12 hours with 10 stages, as shown in Table 2. FIG. 6 shows the liquid stage compositions of lactose and ethanol in the 8-stage MSRS based on a 3-stage enricher and 5-stage stripper. Thus, even for a reaction that can easily be accomplished with no separation, adding separation provides an unexpected, marked improvement in performance. This increase in performance is even more pronounced in actual operation, since cell death rates are a function of ethanol levels (Leao and VanUden, Biotechnol. Bioeng. (1982) 24, 1581) and, in reactors having a high level of ethanol, high cell mortality is found. Data presented (Ryu et al., Eur. J. Appl. Microbiol. Biotechnol. (1982) 15, 1) for cells immobilized on wood shavings in a 6-stage CSTR show cell viability declining from 76% to 28% from stage 1 to stage 6 for the immobilized cells, and from 100% to 75% for the free cells, in the same system, as ethanol concentrations are increased from 60 to 130 g/l. Thus total CSTR performance is generally poorer than that shown in Table 2 which is based on the assumption of 100% cell viability. In the MSRS, however, ethanol levels are maintained at under 50 g/l allowing high cell viability to be maintained indefinitely.

EXAMPLE 2

Figure 7:
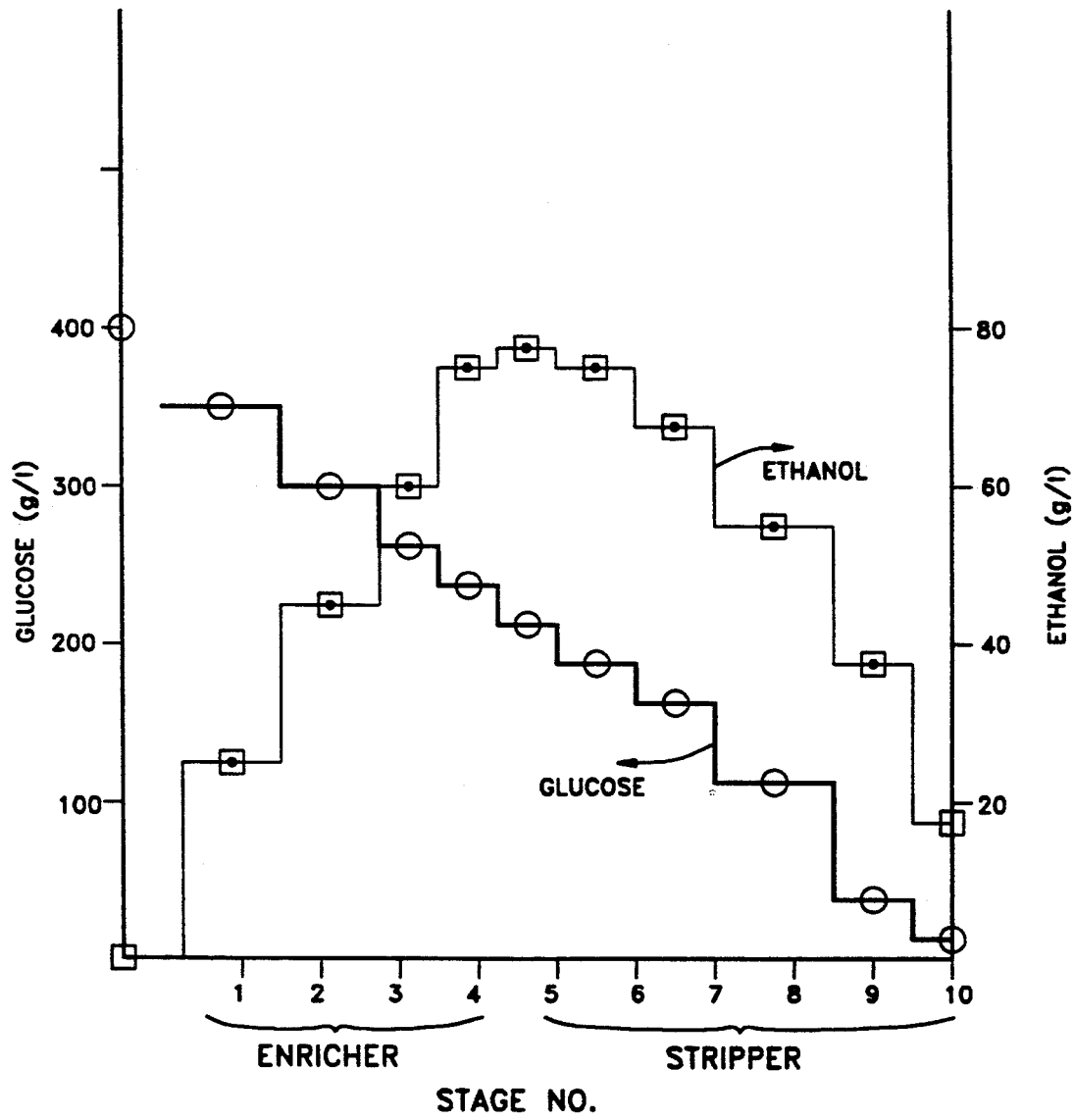
FIG. 7 is a graphical representation of stage profiles for a 10-stage MSRS (Example 2).

The advantages of the MSRS are also clearly evident with either more strongly product inhibited fermentations or high feed substrate concentrations. Conventional glucose-to-ethanol fermentations, either batch or continuous, are unable to utilize substrate levels over 200 to 250 g/l as total product inhibition occurs at 10 to 12% ethanol. The inhibition level varies from species to species with different products and substrates. An MSRS runs with a product concentration well below the inhibition level, since the product is constantly being removed from the system. Using the MSRS of the invention, high substrate levels are also easily handled as product inhibition is avoided by continuous product separation and removal. Although the fermenting cells may be slowed by high initial levels of substrate, the fermentation will still proceed rapidly. High levels of substrate greatly reduce the volume of effluent and favorably impact on the economics of feed preparation and effluent handling, particularly when grain or molasses is used as a feedstock. For example a 400 g/l solution can easily be handled in an MSRS. Using the kinetic equation and values from Table 3, which include a substrate inhibition term, and the same reactor dimensions and operating temperatures as in Example 1, near complete substrate utilization is achieved with a residence time of 9.9 hours in a 10-stage MSRS (4-stage enricher, 6-stage stripper). FIG. 7 shows stage concentration profiles determined for this system using a gas/liquid molar flow ratio of 3.0 in the enricher and 8.0 in the stripper.

TABLE 3

Reaction rate expression (according to Genon et al., Chem. Eng. Commun. (1983) 23, 245).

$$r = X_s v_{max}\left(1 - \frac{P}{K_p}\right)\left(\frac{S}{K_{s1} + S + S/K_{s2}}\right)$$

where:
$X_s$ = 50 gram/liter
$v_{max}$ = 0.85 gram ethanol/gram cell-hr
$K_p$ = 107 gram/liter
$K_{s1}$ = 4.3 gram/liter
$K_{s2}$ = 2300 (gram/liter)$^2$
r = gram ethanol/liter-hour

EXAMPLE 3

The ability of the MSRS to handle insoluble solids and non-fermentable substrate precursors, such as corn grits and cellulose, allows simultaneous saccharification of starches or cellulose during fermentation. The removal of sugars increases the rate of enzymatic conversion of both starch to glucose and cellulose to simple sugars and ensures complete utilization of the total carbohydrate. These polysaccharides may be broken down into fermentable simple mono- and di-saccharides through enzymatic or chemical cleavage of the polysaccharide molecule by the use of, for example, glucoamylase, cellulase or acid. Enzymes may be immobilized in the fermenter, recycled from the effluent, or continuously added to the inlet of the reactor. A process is shown in FIG. 8 for the simultaneous fermentation and saccharification of a gelatinized corn starch feed.

A corn grit feed is gelatinized through a cooking process which allows a low moisture gelatinized starch to be produced. Such methods include the use of steam injected starch cookers and extruders. Downs et al. (Paper #82-3597 ASAE 1982 Winter Mtg, Chicago, Ill.) show that cooking corn grits in an extruder process gives a higher conversion of the starch to fermentable sugar than using conventional batch cooking procedures. The resulting low moisture gelatinized corn starch stream is introduced to the first stage of the MSRS. Water or recycled broth from the effluent is added to obtain the desired level of solids on the stage. Conventional fermenters are limited to solids of 20% or less while the MSRS can handle a 40-50% solids fermentation broth. Enzyme (glucoamylase) is maintained on the stages by (1) continuous addition of fresh enzyme, (2) recycling enzyme from the effluent, (3) immobilizing enzyme in or on beads, pellets or on a stationary support, or (4) a combination of methods (1)-(3). The enzyme converts the starch to glucose, and the glucose, in turn, is converted to ethanol by yeast or bacteria, such as Z. mobilis. Glucose levels are thus kept low on each stage by glucose simultaneously being produced by enzymatic action on the starch while being consumed by the cells converting glucose to ethanol.

Cell density, is maintained similarly to enzyme density through continuous addition, immobilization, recycling of cells, or a combination thereof. The starch is converted to ethanol through a process involving enzymatic hydrolysis of starch to glucose, conversion of glucose to ethanol by cells in the reactor portion of the MSRS, and separation of ethanol from the broth in the gas-liquid contacting portion of the MSRS. FIG. 8 shows a process occurring in an MSRS characterized by a 2-stage enriching section followed by a 4-stage stripping section.

This continuous process offers considerable advantages over conventional batch processes. By fermenting a concentrated feed of starch, the amount of water is reduced considerably. A system may be designed so that the only effluent from the process is a centrifuged feed (Distillers Wet Grain at 70% moisture, or other feed). This represents a considerable reduction in processing costs in all phases of operation: 1) reduced energy requirements for cooking, since little water needs to be heated along with the grain in the gelatinization process, 2) reduced labor and capital cost, since the fermenter is run continuously and is relatively small in size, and 3) greatly reduced waste disposal problems as waste water is reduced to a very low level.

While the invention has been described above with respect to certain embodiments thereof, it will be appreciated that variations and modifications may be made without departing from the spirit and scope of the invention.

What is claimed is:

1. A method for preparing volatile fermentation product from non-volatile substrate comprising:

A. providing a multi-stage reactor-separator having an enriching section comprising at least one stage and a stripping section comprising at least two stages, each of said stages comprising an agitated reactor portion in fluid communication with a gas-liquid separator portion; and charging the reactor portion of each stage with biological catalyst;

B. introducing a feed broth comprising substrate to an agitated reactor portion of a first stage of the enriching section wherein a portion of said substrate is converted by said biological catalyst to form volatile product;

C. contacting liquid outflow broth from the reactor portion of said first stage of said enriching section with a stripping gas introduced to a separator portion of said first stage of the enriching section;

D. introducing liquid outflow from said separator portion of said first stage of said enriching section into the reactor portion of a subsequent stage of said enriching section;

E. introducing stripping gas outflow from the separator portion to the gas-liquid contacting separator portion of a subsequent stage, whereby gas and liquid streams flow co-currently from stage to stage;

F. repeating steps D and E for each stage of the enriching section, whereby volatile product concentrations increase in the liquid and gas streams, and whereby a portion of the substrate is consumed;

G. introducing liquid outflow from a final enriching section separator portion, comprising fermentable substrate and volatile product, into a reactor portion of a first stage of a stripping section in which a portion of remaining substrate is converted to volatile product by biological catalyst and introducing a stripping gas into a separator portion of a final stage of the stripping section;

H. contacting liquid outflow from the reactor portion of a reactor stage with stripping gas moving countercurrently from a subsequent stage in a separator portion of said stage;

I. directing liquid outflow from the separator portion to the reactor portion of said subsequent stage;

J. repeating steps H and I for each stage of the stripping section, whereby product and substrate concentration decrease as the liquid stream moves from stage to stage in the stripper section;

K. separating volatile product from gases exiting the final stages of the enriching and stripping sections.

2. A process of claim 1 wherein biological catalyst density is maintained on each stage by recycling a concentrated stream of biological catalyst from the liquid effluent of the stripping section to the reactor portion of the first stage of the enriching section.

3. A method of claim 1 further comprising maintaining a high concentration of biological catalyst by immobilizing the catalyst on a supporting matrix in the reactor portion and circulating feed broth freely therein.

4. A method of claim 1 wherein the feed broth comprises insoluble solids, and the method further comprises passing said insoluble solids through the system substantially freely without clogging the reactor portion or the gas-liquid contacting separator portion.

5. A method of claim 1 wherein the feed broth comprises substrate and non-fermentable insoluble solids which pass through the multi-stage reactor-separator without clogging the reactor portion or the gas-liquid contacting separator portions of the stages.

6. A method of claim 1 further comprising allowing liquid from a separator portion of one stage to fall by gravity into the reactor portion of a subsequent stage.

7. A method of claim 1 wherein the non-volatile substrate comprises a non-fermentable substrate, the method further comprising converting the non-fermentable substrate to a fermentable substrate.

* * * * *